(12) United States Patent
Mottram

(10) Patent No.: US 6,488,635 B1
(45) Date of Patent: Dec. 3, 2002

(54) ANIMAL EXHALATION MONITORING

(75) Inventor: Toby Trevor Fury Mottram, Chard (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/568,490

(22) Filed: May 10, 2000

Related U.S. Application Data

(62) Division of application No. 08/992,423, filed as application No. PCT/GB96/01464 on Jun. 19, 1999, now Pat. No. 6,129,860.

(30) Foreign Application Priority Data

Jun. 19, 1995 (GB) ............................................. 9512439
Feb. 7, 1996 (GB) ............................................. 9602474

(51) Int. Cl.[7] .............................................. A61B 10/00
(52) U.S. Cl. ................... 600/551; 600/532; 119/14.01; 119/14.14
(58) Field of Search ................................ 600/532, 551; 73/23.3; 422/84; 119/14.01–14.55

(56) References Cited

U.S. PATENT DOCUMENTS

| | | | |
|---|---|---|---|
| 3,910,261 A | | 10/1975 | Ragsdale et al. |
| 4,202,352 A | | 5/1980 | Osborn |
| 4,325,028 A | * | 4/1982 | Takahashi ................ 119/14.14 |
| 4,385,590 A | * | 5/1983 | Mortensen ............... 119/14.01 |
| 5,042,501 A | | 8/1991 | Kenny et al. |
| 5,060,656 A | | 10/1991 | Howard |
| 5,246,010 A | | 9/1993 | Gazzara et al. |
| 5,265,618 A | | 11/1993 | Zimmerman |
| 5,285,794 A | | 2/1994 | Lynch |
| 5,573,005 A | | 11/1996 | Ueda et al. |
| 5,666,903 A | * | 9/1997 | Bull et al. ................ 119/14.01 |
| 5,697,326 A | * | 12/1997 | Mottram et al. ......... 119/14.14 |
| 5,873,323 A | * | 2/1999 | Van Den Berg et al. .. 119/14.02 |

FOREIGN PATENT DOCUMENTS

| | | |
|---|---|---|
| EP | 392503 | 4/1989 |
| EP | 549266 A2 | 6/1993 |
| EP | 650051 A2 | 4/1995 |
| GB | 2272273 | 5/1994 |
| GB | 2272626 | 5/1994 |
| WO | 90/14043 | 11/1990 |
| WO | 92/22813 | 12/1992 |
| WO | 94/07135 | 3/1994 |
| WO | 95/08113 | 3/1995 |

* cited by examiner

Primary Examiner—Robert L. Nasser
(74) Attorney, Agent, or Firm—Pillsbury Winthrop LLP

(57) ABSTRACT

Apparatus and a method for monitoring animal exhalation, to provide an indication of the condition of an animal is disclosed. Apparatus for collection and temporary or permanent storage of animal exhalation sample is disclosed, together with apparatus for conditioning a sample prior to analysis. A method of conditioning a sample prior to analysis is also disclosed. Use may be made of the above mentioned apparatus and method in the diagnosis of the condition of an animal. Conditions of interest include metabolic conditions of animals such as dairy cattle; these can be monitored by measuring analytes in the exhaled breath, emanations from the milk or both. Use may also be made of said apparatus and method in the detection of antibodies present in samples of blood, milk and mucus particulates in exhaled breath. It is preferred that the monitoring apparatus is portable.

6 Claims, 5 Drawing Sheets

ANIMAL EXHALATION MONITORING

This is a division of application Ser. No. 08/992,423, filed Dec. 18, 1997, now U.S. Pat. No. 6,129,680 which was a continuation of International Application No. PCT/GB96/01464 filed Jun. 19, 1996, which designated the U.S.

The present invention relates to the monitoring of the exhalation of an animal in order to provide information about the animal. The information can relate to health, diet or other condition. The animal can be farm livestock such as cattle, domesticated animals such as cats, dogs and horses or poultry such as turkeys and chickens.

Animals produce exhalations some of which are odours such as those from the skin, breath, milk and solid and liquid waste products. It is important that any monitoring is based on an accurately taken sample.

GB 2272773A discloses a method for the examination of the condition of a ruminant animal including sampling odours from at least one part of the animal with an olfactory sensor thereby to identify a specific aspect of the animal condition and apparatus to examine a ruminant animal including means to collect breath or other flow containing an odour of the animal as a sample, means to purge said collecting means, sensing means to receive said sample and identify at least one specific condition of the animal and means to supply an indication of said condition. The method and apparatus may be used to detect conditions such as oestrus, ketosis and other metabolic disorders of ruminant animals in general.

GB 2272626A discloses the use of an olfactory sensor for the checking of any residual contamination after a teat cleaning operation. Purge air or gas can be used.

It is an object of the present invention to provide an effective technique for monitoring livestock on the basis of exhalation from the livestock. Exhalation includes breath from the animal, vapour from milk or any other volatile materials emanating therefrom. Condition can be determined from a component of the exhalation, which component may be an odour or specific compound or other material. The composition of such exhalation can provide a valuable source of information regarding the animal's state of health. The determination of the presence of a particular component in the exhalation can be used to identify an animal's condition.

In a first aspect of the present invention there is provided apparatus for collecting an exhalation sample comprising a housing having inlet and outlet means; a flow path between the inlet and outlet means; and a collapsible container positioned within the housing and in communication with said flow path; means for introducing the sample to the apparatus and means for expelling the sample from the apparatus. It is particularly preferred that the means for introducing the sample to and expelling the sample facilitate flow into and out of the collapsible container.

In a first preferred embodiment the housing comprises a rigid tube having first and second ends, in communication with the flow path at the first end and at the second with means for facilitating the introduction or expulsion of the sample from the apparatus. The rigid tube is preferably made of plastic or other similar material. It is especially preferred that the end in communication with the flow path comprises inlet means for admitting the sample to the apparatus and outlet means for its expulsion. The tube is preferably sealed to prevent the ingress of unwanted contaminants. Sealing is conveniently effected by the use of closures, positioned at the open ends of the tube and appropriately pierced to accommodate the inlet and outlet means, the means for introducing and the means for expelling the sample (exhalation means) from the apparatus.

The collapsible container may take any form appropriate to permit collection and temporary storage of the sample. It is preferred that the container be made of inert material to prevent contamination of the sample. It is especially preferred that the collapsible container is disposable.

The means for introducing and means for expelling the sample from the apparatus may have the effect of facilitating flow of exhalation through the apparatus.

In a second preferred embodiment of the first aspect of the invention the collapsible container comprises a length of plastic tubing, sealed at one end and in communication with the flow path at the other. Typically the type of plastic tubing used for packaging food is preferred.

The means for introducing the sample to the apparatus preferably produces a reduced pressure within the housing in the region surrounding the collapsible container. The establishment of this reduced pressure causes the collapsible container to expand from the collapsed state and thus draw or facilitate the flow of exhalation through the inlet and into the collection apparatus. It is preferred that flow of exhalation is into the collapsible container.

The means for expelling the sample, the exhalation means, from the apparatus preferably produces an increased pressure within the housing in the region surrounding the collapsible container. The establishment of this increased pressure causes the resilient, collapsible container to collapse which forces the exhalation to be expelled, via the outlet, from the collection apparatus.

The inlet and outlet means may be formed integrally or independent of each other and are preferably constructed of inert material to avoid contamination of the sample. The inlet and outlet means are optionally provided with valve means to selectively control the direction of flow of sample into or out of the apparatus. A two way valve may be provided in cases where the inlet and outlet means are formed integrally; the direction of flow of the exhalation sample either into or out of the apparatus may be regulated by use of electronic control means.

A third preferred embodiment of the first aspect of the invention provides apparatus for collecting an exhalation sample comprising a housing with inlet and outlet means; a flow path between the inlet and outlet means; a collapsible container positioned within the housing and in communication with said flow path; means for introducing the sample to the apparatus; means for expelling the sample from the apparatus and means for controlling the direction of flow of exhalation into or out of the apparatus.

Sensing means may also be provided to detect the presence of exhalation. For example flow sensing means may also be provided to detect the flow of exhalation. These flow sensing means may be connected to a central control unit where upon detection of a flow of exhalation, actuation of the sample introduction means occurs thereby effecting flow of the exhalation into the apparatus. The use of sensing and control means facilitates the collection of samples upon detection of exhalation only. These sensing and control means may also be able to distinguish between exhalations derived from the rumen and those derived from the lungs. Actuation of the sample introduction means may also be effected in response to non-rumen derived exhalations.

A fourth preferred embodiment of the first aspect of the invention provides apparatus for collecting an exhalation sample comprising a housing having inlet and outlet means; a flow path between the inlet and outlet means; a collapsible container positioned within the housing and in communication with said flow path; means for introducing the sample to the apparatus; means for expelling the sample from the apparatus; means for controlling the direction of flow of exhalation into or out of the apparatus; flow sensing means and actuation means for facilitating collection of a sample upon detection by the flow sensing means of the flow of exhalation.

In some instances it may be necessary to control the temperature of the collected sample in order to prevent loss of components by, for example, condensation onto the walls of the container. Thus in a fifth preferred embodiment of the first aspect of the invention temperature control means are further included in the apparatus. Such temperature control means may take the form of an electrical heating element, a thermostatically controlled water jacket or equivalent which surrounds or forms part of the housing.

The sample collection apparatus may form part of an apparatus such as an animal condition monitor or it may be in independent form, preferably portable. In either case it is suitable for use in the collection and temporary storage of samples for subsequent analysis. Thus the invention also provides a method of sampling animal exhalation. Such a method comprises the steps of collecting a sample of animal exhalation and storing it for subsequent analysis. Preferably the collection of the sample is in response to the detection of flow of animal exhalation by the flow sensing means. It is especially preferred that the collection of the sample is in response to the detection of non-rumen exhalations by the flow sensing means.

A second aspect of the invention provides an animal condition monitor which comprises inlet means for animal exhalation and any conveying medium; outlet means; a flow path between said inlet and outlet means; detecting means for identifying the presence and/or amount of one or more components of the exhalation (henceforth known as component detecting means); flow assisting means; signal processing and power control means wherein the output of the monitor provides an indication of the condition of the animal.

Preferably the invention further comprises, in its second aspect, sample collection means for collection and temporary storage of the sample. Sample collection means of the type described in the first aspect of the invention are preferred. The sample collection means are preferably included in and are open to or in communication with the flow path of the animal condition monitor.

In a first preferred embodiment of the second aspect of the invention there is provided an animal condition monitor which comprises inlet means for animal exhalation and any conveying medium; outlet means; a flow path between said inlet and outlet means; sample collection means for collection and temporary storage of the sample; component detecting means; flow assisting means; signal processing and power control means wherein the output of the monitor provides an indication of the condition of the animal.

The flow assisting means may be provided instead of or in addition to the sample introduction and/or the sample exhaustion means provided by the apparatus for collection of the sample according to the first aspect of the invention. Conveniently such flow assisting means are present within the flow path. It is especially preferred that actuation of the flow assisting means is in response to the detection of flow in the flow path of the apparatus.

Flow sensing means may also be provided. These are preferably positioned within the flow path. The output from the flow sensing means is preferably fed to the signal processing and power control means. It is especially preferred that actuation of the flow assisting means is effected in response to the detection of flow by the flow sensing means. Actuation of the component detecting means may also be effected in this way.

The determination of the condition of an animal is best effected by measurements made on exhalations emanating from the lung, preferably alveolar derived exhalations, rather than those of the rumen. It is therefore preferable to collect exhalations from the lung rather than from the rumen.

A second preferred embodiment of the second aspect of the invention further provides selective means for distinguishing between rumen and non-rumen exhalations. The output from the selective detection means is preferably fed to the signal processing and power control unit. In this way the operation of the apparatus can be controlled so that actuation of the monitor is only effected upon the detection of non-rumen exhalations. In this way it is possible to monitor only those exhalations of interest.

The choice of component detecting means will be apparent to a skilled person. Typically, these component detecting means should be sufficiently robust to withstand the conditions employed during sampling. These component detecting means are preferably placed within the flow path whereby contact with the sample is effected. They should provide an output in the form of an electrical signal or one capable of being converted thereto. They should have a relatively short response time to allow rapid determinations to be made. The response should also be reproducible. Electrochemical detectors or detectors derived from conducting polymers are preferred.

An accurate indication of the condition of the animal may depend upon the physical condition of the sample and in this respect it may be advantageous to control aspects such as the temperature, pressure, humidity, velocity and extent of dilution of the sample either individually or in combination. The provision of a purge or carrier gas (dilution means) may also be of advantage since this may also be used to standardise the physical condition of the sample.

Additional embodiments of the second aspect of the invention provide, either individually or in combination, temperature controlling means, humidity controlling means, pressure controlling means, sample velocity control means, sample dilution means and means for monitoring and controlling the extent of the dilution. The reproducibility of the component sensors is generally increased by standardising the sample. The results obtained are therefore more likely to be reliable and provide a good indication of the condition of an animal.

In order to ensure good reproducibility it may be necessary to purge the apparatus between determinations. The choice of purge gas will depend upon the component detector means and the nature of the sample. Examples of gases used for purging include bottled air or an inert gas such as nitrogen.

A third embodiment of the second aspect of the invention further provides means for purging the apparatus between determinations. The length of the purging cycle may vary but should be long enough to allow the response of the component detecting means to return to its baseline value. Ideally the component detection means should be exposed to the sample for the same length of time as it is exposed to the purge gas. This gives the component detecting means the same length of time to adjust to both the sample and purge environments optimising the response times for each.

A fourth preferred embodiment of the second aspect of the invention further provides exhaustion means for expelling the exhalation sample and any conveying means from the monitoring apparatus. Typical exhaustion means will be apparent to a person skilled in the art. Exhaustion may be effected by use of a purging gas. Alternatively, use may be made of components such as impellers, fans, pumps and the like to expel the sample and any conveying medium from the apparatus.

The condition or the state of the sample is preferably standardised by the use of physical means. This generally has the effect of ensuring that the output from the component detecting device is both reproducible and provides an accurate indication of the state of the sample. However, by processing the signal from a non-standardised sample an output can be obtained which is both reproducible and meaningful. It is preferred that such signal processing is carried out with reference to the physical conditions within the apparatus at that time. In this way a correction may be applied to account for any nonstandard conditions and physical manipulation of the sample is not then required.

A fifth embodiment of the second aspect of the invention provides an animal condition monitor including a monitor inlet for animal exhalation (as herein defined) and any conveying medium, a flow path from said inlet for said exhalation and any medium, a monitor flow sensor for the exhalation and any conveying medium flow path to provide a flow indicating signal, the flow path including a sensor to provide a condition indication signal, together with means to assist flow in said flow path, the monitor further including signal processing and power control means responsive to the signals and a power source to provide condition indication output on a suitable flow signal.

It is preferred that the animal condition monitor includes an inlet for animal exhalation (as herein defined) and any conveying medium; a flow path from the inlet which comprises sensing means for monitoring and indicating flow of the exhalation and optionally the conveying medium, detecting means for identifying the presence and/or amount of one or more components of the exhalation (henceforth known as component detecting means) of the animal and flow assisting means; signal processing and power control means responsive to the output from the sensing and detecting means and a power source, wherein the output of the monitor provides an indication of the condition of an animal. The indication of the condition of the animal may be included in a method in which further processing steps are required to establish the condition of an animal; or the indication may need to be interpreted by a skilled person in order that the condition of the animal be established.

A sixth preferred embodiment of the second aspect of the invention provides an animal condition monitor including a monitor inlet for animal exhalation (as herein defined) and any conveying medium, a flow path from said inlet for said exhalation and any medium, an exhalation and medium collector housing connected to said flow path, a collector retainer for a replaceable, collapsible, sized collector, open to said flow path, means to assist flow to an adequate level in said flow path into a retained collector, the arrangement being such that animal exhalation and any conveying medium can be drawn into a retained collector from said inlet as a sample.

It is further preferred that the animal condition monitor includes an inlet for animal exhalation (as herein defined) and any conveying medium; a flow path from said inlet; a housing in communication with and open to said flow path, adapted for collection of the exhalation and other medium; flow assisting means to ensure transfer of the exhalation and conveying medium (as a sample) from the inlet, through the flow path and into the housing; characterised in that the housing further includes a resilient, collapsible container positioned within the housing and open to the flow path. It is especially preferred that the container is disposable.

There may be means to displace from the collector animal exhalation and any conveying medium drawn into a collector for sensing by a condition sensor. An exhalation component sensor, optionally in the form of a sensor adapted to be sensitive to particular chemicals is preferably present to provide an indication of odour output. Means for maintaining a selected temperature, pressure and/or humidity level in the monitor are preferably provided.

The flow assisting means in the flow path may include at least one impeller movable in the flow path. The means to assist flow in the flow path preferably produces a reduced pressure in said flow path. The means to produce a reduced flow path pressure preferably produces a reduced pressure around said retained collapsible container.

Exhaustion means are preferably provided to transfer the exhalation (as herein defined) and conveying medium from the apparatus. In one embodiment the component detecting means for indicating the condition of the animal is placed in the exhaust path. It is preferred that means for maintaining a selected temperature and/or humidity level in the monitor are also present.

Preferably the flow assisting means include at least one impeller movable in the flow path. The flow of the sample in the flow path may be effected by the production of a, reduced pressure, preferably around the collapsible container.

In addition, means may be provided for monitoring and controlling the temperature, pressure and/or the humidity of the exhalation (as herein defined) and conveying medium in the monitoring apparatus. In some instances it may be desirable to include or introduce a known quantity of a calibration gas into the sample thereby allowing the temperature, pressure, humidity and rate of flow of the sample mixture to be controlled; such a process is known as dilution. Optimal results can be achieved by passing the sample mixture over the component detecting means at a predetermined temperature, pressure, humidity and flow rate and comparing the response of the component detecting means to that observed during the passage, between samples, of a calibration and purging gas mixture under similar conditions. This ensures standardisation of the sample with respect to the calibration mixture.

A seventh preferred embodiment of the second aspect of the invention provides an animal condition monitor which includes a monitor inlet for animal exhalation (as herein defined); flow sensing means; means for introducing the conveying, calibration and purging means into the apparatus; means for monitoring the temperature and/or humidity of the sample; means for controlling the temperature and/or humidity of the sample within the apparatus; means to monitor and/or control the dilution of the sample within the apparatus; component detecting means adapted to be responsive to specified components within the sample; a flow path from the inlet for the sample or sample mixture; flow assisting means; a power source and output means to provide an indication of the condition of the animal from the response of the sensing means.

Component detecting means adapted to operate in the ambient environment may be used. Preferably these component detecting means are capable of distinguishing the components of interest within the sample from the background environment. Electrochemical detectors are especially preferred.

As the soft palette of an animal is always likely to open, which opening allows unwanted rumen gas such as methane to enter the monitor, care must be taken as high concentrations of methane can affect measurements. It is preferred that emanations not originating from the rumen are sampled. Emanations of particular interest are those arising from the lungs and milk.

Exclusion or minimising the amount of rumen gas in the sample may be achieved by monitoring exhaled breath. It is preferred that the means for introducing the conveying and/or calibration medium and/or the flow assisting means are actuated by part of the animals breathing cycle eg conveniently by detection of the animals exhaled breath. Such actuation may be in response to the output of the flow detecting means.

An eighth preferred embodiment of the second aspect of the invention provides an animal condition monitor substantially as herein described wherein the operation of the apparatus is activated by the flow of animal exhalation. Preferably the activation is initiated by the flow sensing means.

A monitor is preferably arranged to receive only exhaled breath of an animal.

Conveniently the replaceable, collapsible sized collector is a set length of set cross-section food quality plastic tube.

The flow path to the collector may include a one-way valve to allow flow only into the collector from the inlet and the flow path may then extend past the sensor to an outlet, the monitor also including means to assist flow from the collector to the outlet.

The sensor may be downstream from the monitor inlet. The monitor may be arranged to be inserted into a nostril of an animal. The monitor may be arranged to respond only when adequate animal exhalation occurs.

The monitor may be arranged to be inserted into a milk flow system such as a whole or quarter milker to receive odour by the action of the vacuum of the system. It is preferred that the monitor inlet is positioned such that the animal exhalation can be readily collected. The inlet may be in communication with a tube, adapted for positioning within the animal's nostril. Alternatively the inlet may be incorporated in or adjacent to the animal's feeding trough or be included as part of the milking arrangement.

The monitor is preferably of chemically inert material, at least where contact with exhalation can occur.

There may be at least one further odour sensor downstream of a first odour sensor. Components sensed may include those of ketosis, that is acetone in breath or milk, and mastitis pathogens by composition/odour of milk. One or more component detecting means may be placed within the flow path. These may be placed individually or as an array; together, sequentially or at predetermined positions within the flowpath.

Means may be provided to "wash" sensors or component detecting means to aid recovery of detection ability. Preferably, the washing comprises the passage of purge and/or calibration gas over the sensors or component detecting means between samples. Alternative temperature and humidity conditions to those used during normal operating conditions may be employed to assist in the removal of any contaminants from the sensors.

A reference exhalation component may be provided for a sensor.

The invention also provides a method of monitoring animal exhalation.

A third aspect of the invention provides a method of monitoring animal exhalation comprising the steps of isolating said animal exhalation, contacting the exhalation with component detecting means, monitoring and recording the response of the component detecting means and determining the condition of the animal therefrom.

The use of electrochemical detectors is preferred. Electrochemical detectors can vary their output with temperature, pressure, humidity, air flow and pressure which may mask signals generated by components of interest within the sample or sample mixture. In order to obtain reproducible results it is desirable to maintain the temperature, pressure, humidity, air flow and pressure of the sample or sample mixture within a specified range. The use of a calibration medium is especially preferred since this facilitates the establishment of reference and control values with which the component detector output for the sample or sample mixture may be compared.

A first embodiment of the third aspect of the present invention comprises the steps of isolating animal exhalation; monitoring the temperature, pressure, humidity, pressure and velocity of the isolated animal exhalation; admixing with the exhalation, if required, a known quantity of conveying and/or calibration medium and heating or cooling the resulting sample or sample mixture to maintain the temperature, pressure and humidity within a specified range; passing over the component detecting means a mixture of a calibration and purging medium the composition, temperature, humidity, pressure and velocity of which is within specified values; recording the response of the component detecting means to the calibration and purging medium mixture and determining a baseline response therefrom; passing over the component detecting means the treated sample, the temperature, humidity, pressure and velocity of which is within the same specified values as that of the calibration and purging mixture; recording the response of the component detecting means to the sample mixture; comparing the baseline response with the sample response thereby providing an indication of the condition of the animal; and passing a purge gas over the component detecting means at a reduced pressure until the response of the detecting means corresponds to the aforementioned baseline response. It is preferred to expose both the calibration and purging medium mixture and the sample mixture to the component detecting means for similar periods of time. The indication of the condition of the animal may be included in a method in which a signal processing step is used to establish the condition of an animal; or the indication may need to be interpreted by a skilled person in order that the condition of the animal be established.

A fourth aspect of the invention provides apparatus for treatment of an animal exhalation sample prior to analysis comprising inlet and outlet means, a flow path between the inlet and outlet means and means for conditioning the sample. The treatment of the exhalation sample prior to analysis facilitates standardisation of the sample. The results of determinations made using a standardised sample are generally thought to be more reliable as any variations in the response of the component detecting means arising from differences in the temperature, pressure, humidity etc of the sample are eliminated and the measured response will be representative of the composition of the sample.

Conditioning the sample may include controlling each of the temperature, pressure, humidity, flow velocity and dilution, either individually or in combination. Depending upon the requirements, it may not be necessary to control all of these physical parameters and the form of the conditioning means will depend upon which of those parameters are considered to be important for the application in question.

A first embodiment of the fourth aspect of the invention provides apparatus for treatment of an animal exhalation sample prior to analysis comprising inlet and outlet means, a flow path between the inlet and outlet means and conditioning means wherein the conditioning means include temperature sensing means and means for controlling the temperature of the sample within the apparatus. The number and position of the temperature sensing means will depend upon the nature of the apparatus but should be sufficient to ensure the detection of any significant temperature variation of the sample within the apparatus. It is therefore preferable to provide temperature sensing means at or near to the apparatus inlet and at or near other positions within the apparatus where manipulation of the sample occurs. The type of means for controlling the temperature will be apparent to a person skilled in the art and include an electrical heating element or a component such as a thermostatically controlled water jacket or equivalent. As with the temperature sensing means, the number and position of such means will depend upon the nature of the apparatus and should be sufficient to ensure that the temperature of the sample does not vary significantly from any predetermined value. It is possible to avoid any significant variations in temperature of the sample by placing the temperature controlling means adjacent to or slightly downstream of any positions within the apparatus where physical manipulation of the sample occurs. It is preferred, in positioning the temperature control means, not to place such means adjacent to the temperature sensing means since this will prevent the accurate determination of sample temperature within the apparatus.

In a second embodiment of the fourth aspect of the invention the conditioning means further includes humidity sensing means and means for controlling the humidity of the sample. Similar considerations apply regarding the number and positioning of the humidity sensing and control means as apply to the temperature sensing and control means referred to in the first embodiment of the fourth aspect of the invention.

It is preferred that the number and position of the temperature sensing means, the temperature control means, the humidity sensing means and the humidity control means is sufficient to ensure that the temperature and/or the humidity of the sample correspond to those values for which the response of any component detecting means used for subsequent analysis is optimum.

In a third preferred embodiment of the fourth aspect of the invention the sample conditioning means includes temperature sensing means, temperature control means, humidity sensing means and humidity control means. The combination of means facilitates manipulation of the state or condition of the sample thereby ensuring an optimum response of the component detecting means on analysis of the sample.

In a fourth embodiment of the fourth aspect of the invention the conditioning means further include dilution means. The dilution means ideally comprise an inert gas such as nitrogen or a mixture of gases of known composition such as high purity air. The use of dilution means may influence the temperature, pressure, humidity and composition of the exhalation sample. It is especially preferred that the temperature and humidity of any dilution means is maintained within a predetermined limit so that any further manipulation of the exhalation sample can also be readily controlled.

Dilution of the sample may be effected upon entry of the sample into the apparatus. At this stage the dilution means may also function as a conveying medium.

It may be desirable to dilute the sample in response to physical changes brought about during the conditioning process. It may also be desirable to dilute the sample as a final step in the conditioning process, prior to its being analysed.

As mentioned previously, the sample may be diluted in order to facilitate control of its temperature, pressure and/or humidity. Dilution of the sample may also be necessary in circumstances where the sample is very concentrated; without dilution of the sample the response of any component detecting means would probably be off the scale and therefore meaningless. The use of dilution means therefore helps to ensure that the results obtained from the analysis of a conditioned exhalation sample are both reproducible and meaningful.

In a fifth preferred embodiment of the fourth aspect of the invention the conditioning means comprises temperature sensing means, humidity sensing means, temperature controlling means, humidity controlling means and dilution means. The use of a combination of means facilitates extensive conditioning of the sample which ensures that reproducible and accurate results are obtained from subsequent analysis of a sample so conditioned.

In a sixth embodiment of the fourth aspect of the invention the conditioning means also comprises pressure sensing means. It is preferred that means to control the pressure of the exhalation sample are also present. The number and position of the pressure sensing and pressure control means will, as indicated above, depend upon the nature of the apparatus and the component detecting means but should be such as to ensure that the pressure of the exhalation sample prior to analysis facilitates an optimum response from the component detecting means.

In a seventh preferred embodiment of the fourth aspect of the invention the conditioning means comprises temperature sensing means, humidity sensing means, pressure sensing means, temperature controlling means, humidity controlling means, pressure controlling means and dilution means.

It is preferred that the output of the temperature sensing means, the humidity sensing means and the pressure sensing means are fed to the power control and signal processing unit. It is especially preferable that the functioning of the temperature controlling means, the humidity controlling means, the pressure controlling means and the dilution means are also controlled via this unit. This allows alteration of the temperature, pressure, humidity and extent of dilution of the exhalation sample in response to the output signals of the sensing means.

In many instances the apparatus for treatment of an animal exhalation sample prior to analysis comprises part of the animal condition monitoring apparatus. It may be desirable to transport the sample within the animal condition monitor out of the sample treatment component thereof so that interaction of the sample with the component detecting means is effected subsequent to its being conditioned. The provision of flow assisting means and optionally exhaustion means facilitates this transport and ensures thorough mixing of the sample.

In an eighth embodiment of the fourth aspect of the invention the conditioning means further includes flow assisting means. Exhaustion means may also be included.

A fifth aspect of the invention provides a method for treating an exhalation sample prior to its analysis comprising the steps of collecting said sample, determining its state and conditioning said sample accordingly. Conditioning the sample may require changes be made to each or a combination of its temperature, humidity pressure and extent of dilution.

Determination of the state of the sample may be effected by measurement from each or a combination of the temperature, humidity or pressure sensing means. Information derived from the sensor output may be used to control the state of the sample.

For conditioning the sample use may be made of each or a combination of the temperature controlling means, the humidity controlling means, the pressure controlling means and the dilution means. Changes to each of these parameters may be invoked by the power control and signal processing means in response to the output from the sensing means.

A preferred embodiment of the fifth aspect of the invention provides a method of treating an exhalation sample prior to analysis which comprises the steps of isolating animal exhalation; monitoring the temperature, humidity, pressure and velocity of the isolated animal exhalation; admixing with the exhalation, if required, a known quantity of conveying and/or calibration medium and heating or cooling the resulting sample or sample mixture to maintain the temperature, pressure, humidity and velocity of the sample within a specified range.

A sixth aspect of the invention comprises the use of the apparatus and method according to each or a combination of the five aspects of the invention herein before described in a method for diagnosing the condition of an animal. Typically the metabolic condition of animals such as dairy cattle can be monitored by measuring analytes in the exhaled breath and milk, and the present invention includes a monitor or method in which the exhalation is either exhaled breath, emanation from the milk or both.

The apparatus described herein above may be incorporated into an animal feed trough. Positioning the apparatus in this way facilitates the collection of animal exhalation samples.

A seventh aspect of the invention comprises an animal feed trough which includes apparatus according to the first, second and fourth aspects of the invention.

The sensing technique may also be use to detect, inter alia, antibodies present in samples of blood, milk and mucus particulates in exhaled breath. It is preferred that the monitoring apparatus is portable since this would facilitate the rapid screening of animals for exposure to pathogens such as brucella aborta.

Preferably the performance of the animal monitor is itself monitored over its period of use and an alternative system of analysis may be employed for this purpose. Gas Chromatography in combination with Mass Spectometry (GCMS) is the preferred alternative and in a preferred embodiment of the fifth aspect of the invention a method is provided which includes the steps of diverting a proportion of the sample mixture from the flow path, passing it through a GCMS system, assessing the output therefrom and comparing it with the output of the animal condition monitoring apparatus.

The apparatus and method of the invention will now be described by way of illustration only by reference to the following non-limiting Examples and Figures. Embodiments of the invention will now be described with reference to the accompanying drawings in which:

FIGURES

FIG. 1 shows schematically in part-sectional form one embodiment of the invention in the form of an animal condition monitor suitable for sampling animal condition by examination of odour from the nostril of, for example, a cow.

Figure 1:
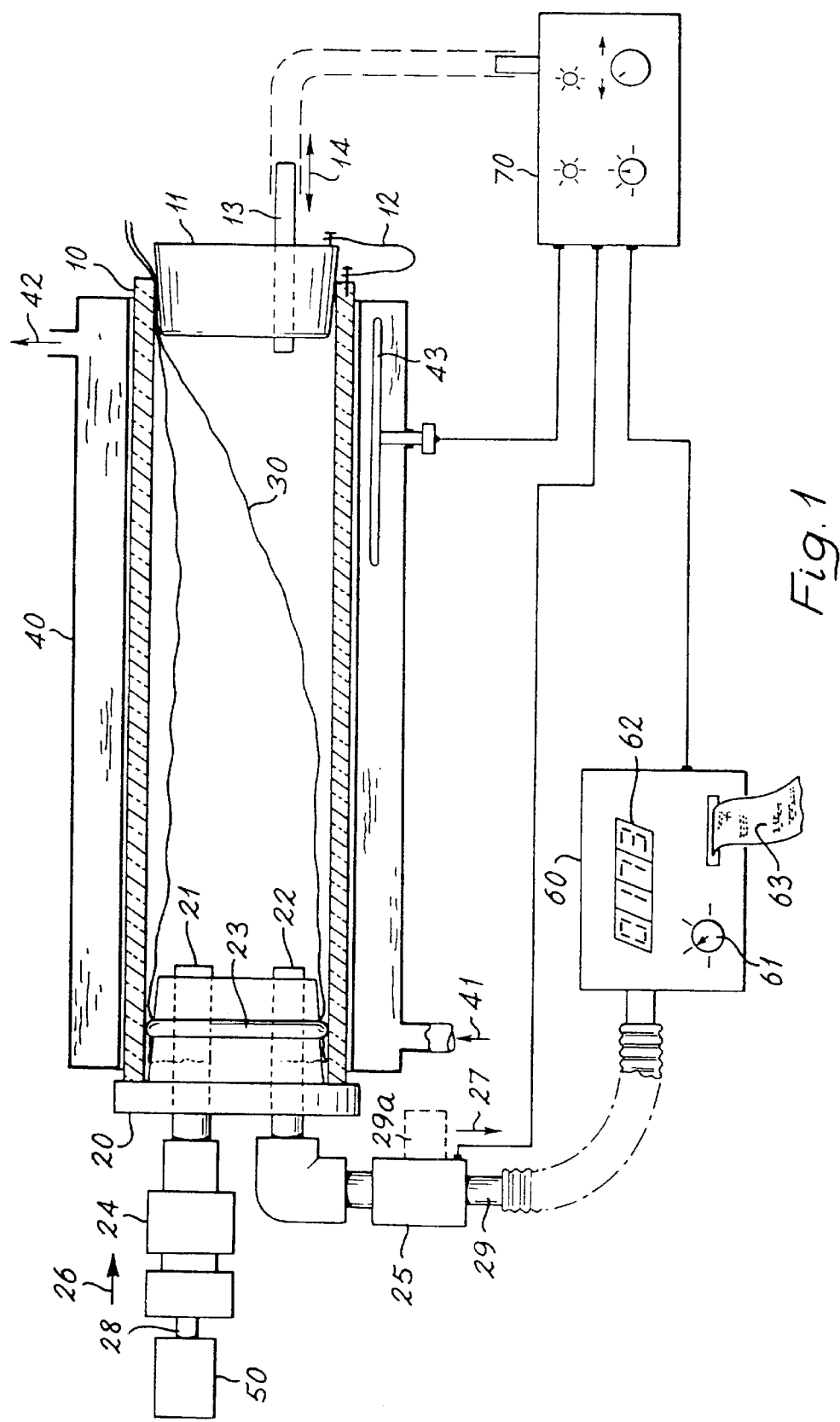
FIG. 1 shows a diagram of one monitor embodying the invention.

The body of the monitor is a tube which is conveniently of a transparent plastics material which is preferably inert and free of odours and easily cleaned. The ends of the tube can be closed in gas-tight manner by closures 11 and 20 to enclose a space. Closure 11 is pierced by a tube 13 through which gas can be withdrawn from or supplied to the space within tube 10.

Conveniently closure 11 is kept attached to tube 10, when not in position, by a retainer 12. Closure 20 is pierced by two tubes 21 and 22 which will be described more fully below. Closure 20 is provided with sealing means engageable with the inside surface of tube 10, such as an O-ring 23, seated in a suitable groove in the closure. Preferably the sealing means is also used to position container 30 within tube 10. The O-ring has a further function with regard to a container 30 which can be placed in the tube 10 in use of the monitor. Container 30 is a length open at both ends of food-quality or similar inert and odour-free transparent plastics of thin and flexible tubular form similar in diameter to the inner diameter of the tube 10 and of slightly greater length. In use closure 20 is placed inside one end of container 30 with the O-ring 23 inside the container and the container placed in the tube and held in place by inserting closure 20 into the end of tube 10, trapping the one end of the container end between the O-ring 23 and tube 10. The container 30 is held in place by closure 11 in such a way as to close the other end of the container by trapping it between the closure and the tube, for example as shown in the Figure, with the container free to inflate and deflate.

The arrangement of closure 20 is now further described. Tube 21 supports outwardly of closure 20 a valve 24 selectively operable to allow flow of gas through closure 20 and into a container 30, when installed as described above. Tube 22 supports outwardly of closure 20 a valve 25 selectively operable to allow flow of gas out of a container 30, when installed as described above, through closure 20.

Temperature control means may be provided to monitor and maintain the temperature of the apparatus as required. Preferably a water jacket 40 surrounding tube 10 is provided. Electrical heating means may also be provided as appropriate.

A temperature-control arrangement exemplified by water jacket 40 can be provided around tube 10. The water jacket can be heated by an electrical heater 43 or temperature adjustment by liquid flow can be used if appropriate. Other temperature-control arrangements will be readily apparent.

Arrow 14 represents the possible gas flow directions through closure 11, arrow 26 the selective gas flow direction through valve 24, arrow 27 the selective gas flow direction through valve 25 and arrows 41 and 42 flow through water jacket 40.

The outlet 29 is connected to a suitable sensor 60 for odours to be monitored. The sensor is conveniently a unit including an element or elements commonly called an electronic "nose" and arranged to be controllable 61 to provide an indication in transient 62 or permanent form 63 of the type and/or concentration of an odour of interest.

Power supply for sensor 60 can be battery or mains as appropriate, and is not shown. Suitable components and circuits will be apparent to those skilled in the art. Instead of the so-called electronic "nose" other analysis techniques such as those based on other sensors, which may use Fast Fourier Transforms of electronic signals or infra-red examination can be applied, as will be apparent to those skilled in the art.

The operation of the monitor is as follows: before operation it is ensured that the monitor is clean and free of any possible contaminants of the exhalation to be monitored. A fresh length of plastics is installed to form container 30. A fresh adaptor 50, to extend the inlet 28 of valve 24 to suit the nostril of a cow to be monitored, is fitted. A moderate gas pressure is produced inside tube 10 by supply of gas under pressure via tube 13. This pressure is arranged to deflate container 30, expelling air via valve 25. The monitor is then ready for use. The adaptor 50 is applied carefully to the nostril of the cow and at a suitable time gas is withdrawn from tube 10 via tube 13 to inflate container 30 to draw gas at an adequate rate from the nostril of the cow through adaptor 50, inlet 28, valve 24 and tube 21 through closure 20 in a flow path to the container 30. When the container is sufficiently full the withdrawal of gas from tube 10 via tube 14 is stopped. Valve 24 is set to be closed or only allow flow in the sense of arrow 26. The adaptor and monitor are removed from contact with the cow. Gas under pressure is then again supplied through tube 14 to inside tube 10 to deflate container 30. Valve 24 prevents gas flow from the container 30 so escape of gas drawn from the nostril of the cow to container 30 is through valve 25 to sensor 60, where appropriate odour indication is provided.

Clearly variations on the above basic operation are possible. For example a "dump" outlet 29a on valve 29 permits an initial part of the gas from the nostril of the cow to be vented before reaching the sensor, which only receives a subsequent part of the gas, in appropriate the withdrawal of gas via tube 14 being delayed.

Other variations are clearly possible, for example constructional adaptations to provide a monitor for use on the teats or other part of the animal whence exhalations are to be examined. Instead of the nostril adaptor a hood or other arrangement may be provided.

If the temperature of the monitor, and the gas to be examined, is important the operation of the monitor can be related to this temperature.

A suitable power conditioning and control unit 70 can be provided to produce and control gas flow at tube 13 and other functions such as heating element 43, sensor 60 and valve 25, if electrically operable. Unit 70 would thus include a pump, preferably of the positive displacement type and, for "field" use, a battery to supply power. Flow direction at tube 13 could be controlled by a manually-operable "in-line" valve if preferred to provide flow in either direction or none at all.

Materials, valve types and constructional techniques will be apparent to those skilled in the art from the above. For the container 30 the proprietary material NALOPHAN (Hoechst AG) is appropriate as this is manufactured to be completely neutral in taste and odour and practically impermeable to aromas, gas and water vapour. In one monitor as described above NALOPHAN tube of material 20 micrometers in thickness was used. The tube size was 49 millimeters in diameter (77 millimeters flat) and of a length of some 400 millimeters.

One important precaution in use of the monitor for cows in particular is the need to avoid opening the soft palette, possibly by excess suction with the monitor, which would allow rumen gas, including methane, to enter the monitor, not the required nostril gas sample. A further precaution may be flow rate indication and any appropriate interlock to ensure that exhalation of breath by the cow is the event monitored and collection of rumen gas is avoided.

Figure 2:
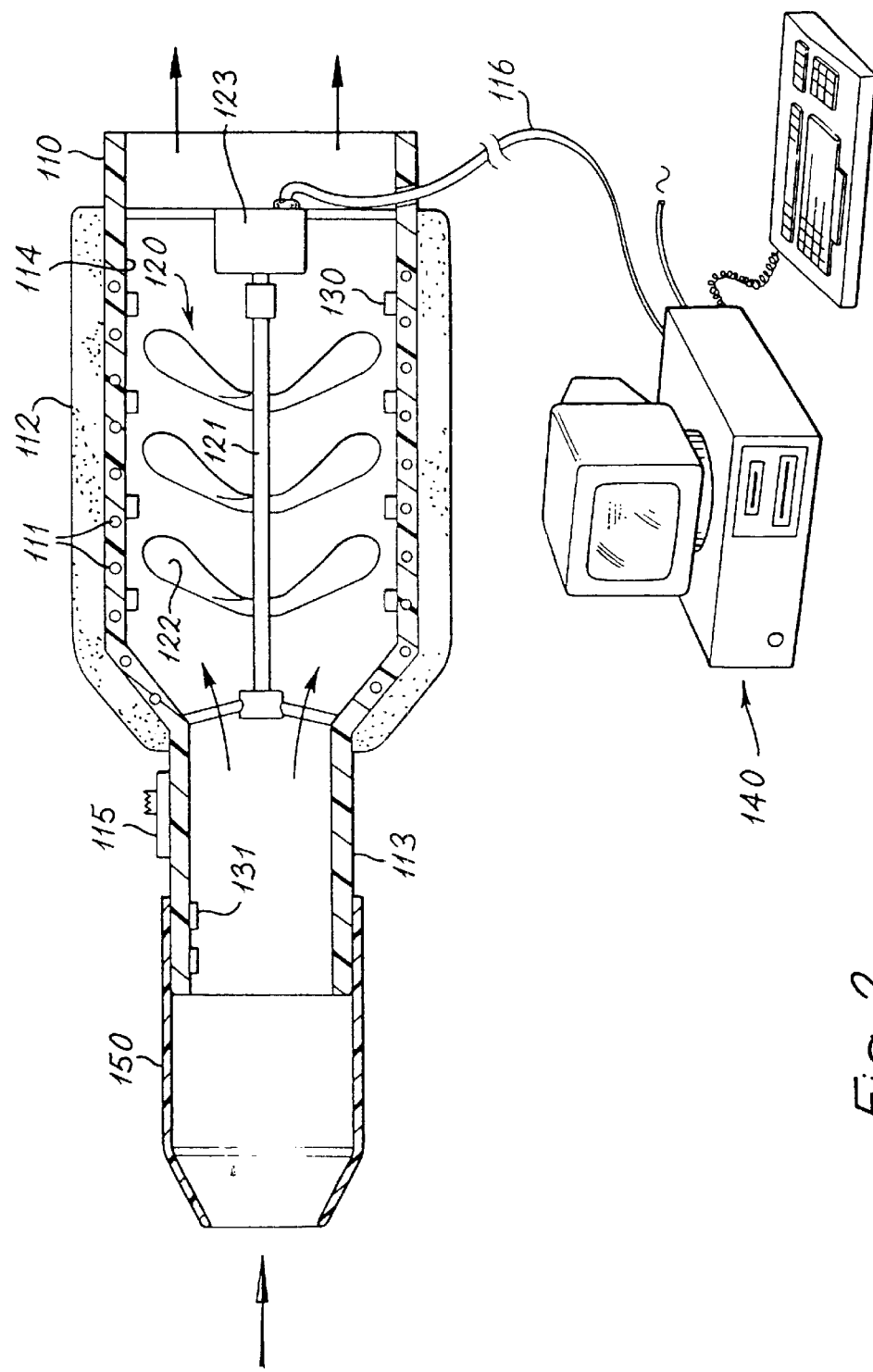
FIG. 2 shows a diagram of another monitor embodying the invention.

FIG. 2 shows schematically and in part-sectional form another embodiment of the invention in the form of an animal odour monitor suitable for sampling animal odour from the nostril of, for example, a cow.

The body 110 of the monitor is formed to be hand-holdable, of generally cylindrical form, with a tapered inlet 113 having a replaceable extension 150 to fit the nostril of a cow.

As it is preferable for the sensors to be operated in the region of 40° C. the body 110 includes electrical heating elements 111 embedded therein. The hand-holdable part is covered with a heat-insulating layer 112 to retain the heat and be cool to the touch. The heating is conveniently thermostatically controlled.

To encourage the flow of gas from the nostril through the inlet 113 in a flow path past the sensors the monitor body supports a fan assembly 120 of an axially disposed shaft 121 and several blades 122 arranged to direct gas in the flow path towards odour sensors 130 mounted on faces of planar surfaces 114 on the inside of body 110. The fan is driven by a motor 123 connected to shaft 121.

To determine if the flow rate is adequate and in the correct direction a thermistor flow sensor 131 is mounted in the inlet 113.

The various portions of the monitor are electrically operated and power is supplied by use of a multiway connector 116 which also conveys signals from the flow sensors 131 and odour sensors 130. An on-off switch 115 is provided at a convenient position.

A suitable arrangement for controlling the monitor and displaying the results of operation is a personal computer 140 of generally conventional form.

The control arrangement ensures that sampling is effective when the monitor is on and the animal is exhaling. Suitable materials will be readily apparent. The monitor body should be of chemically inert material to avoid stray odours and aid cleaning.

Figure 3:
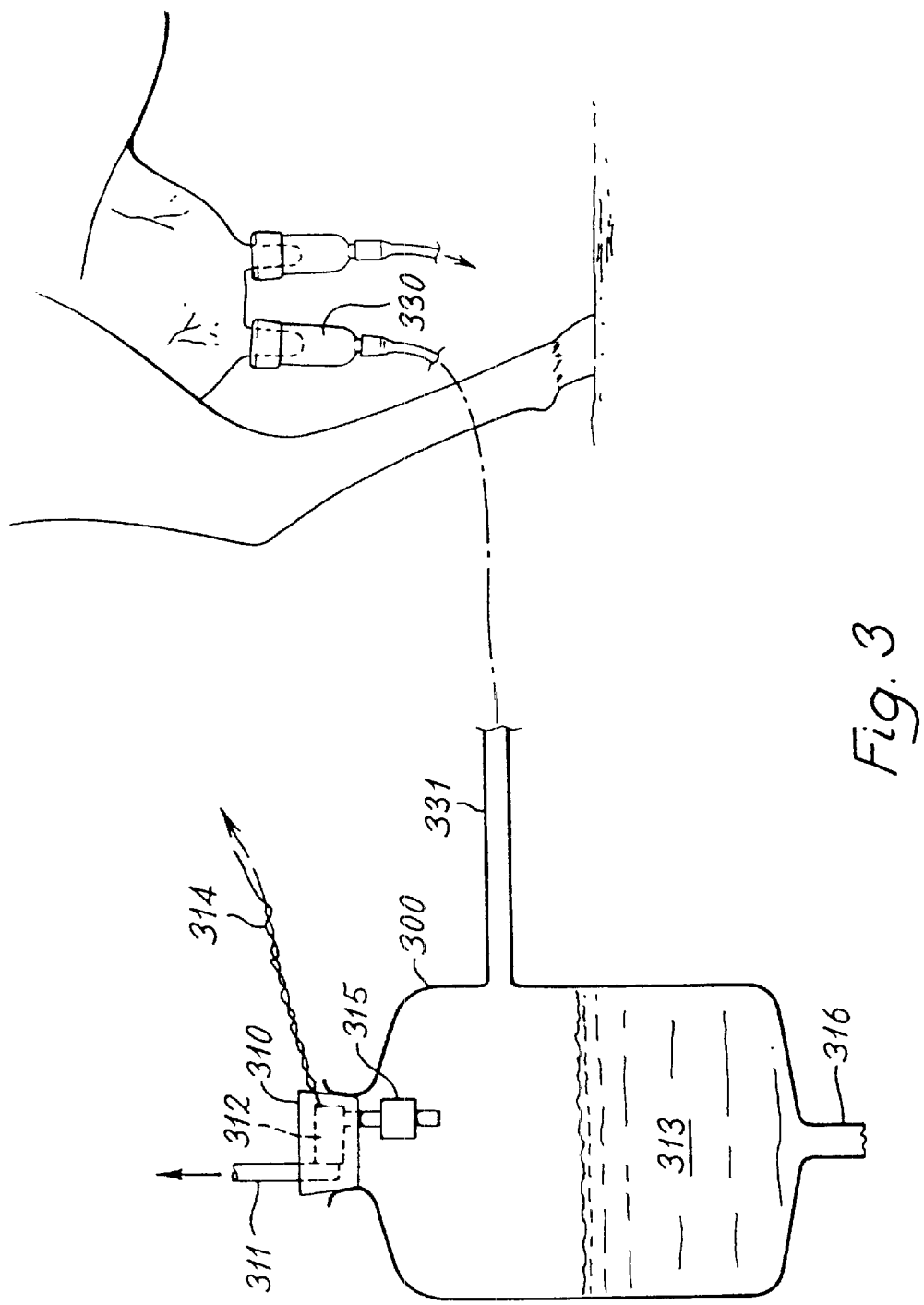
FIG. 3 shows a diagram of a further monitor embodying the invention.

FIG. 3 shows a further form of monitor suitable for use in a milking line to sample odour from milk contained in the line. The milk may be contained in a milking jar of a milker of the whole or quarter milker type or in a milk meter.

For example a quarter milker jar 300 may have an odour sensor 312 fitted in the vacuum connection 310. The jar 300 is conventionally connected (not shown for clarity) to a teat cup 330 as is well-known and will not be described further. Milk from a teat to which the teat cup is attached passes over a connection 331 to milk jar 300 under the influence of a vacuum applied at 311, in conventional known manner. The vacuum is effective to draw odour from the milk 313 in jar 300 past the sensor 312 and signals indicating odour nature and amount supplied over electrical connection 314 to utilisation means of any convenient form. A valve 315 is provided to protect the sensor during washing of the milk jar. In another arrangement the sensor 312 can be retracted to protect it. Milk can be released from the jar via connection 316.

Figure 4:
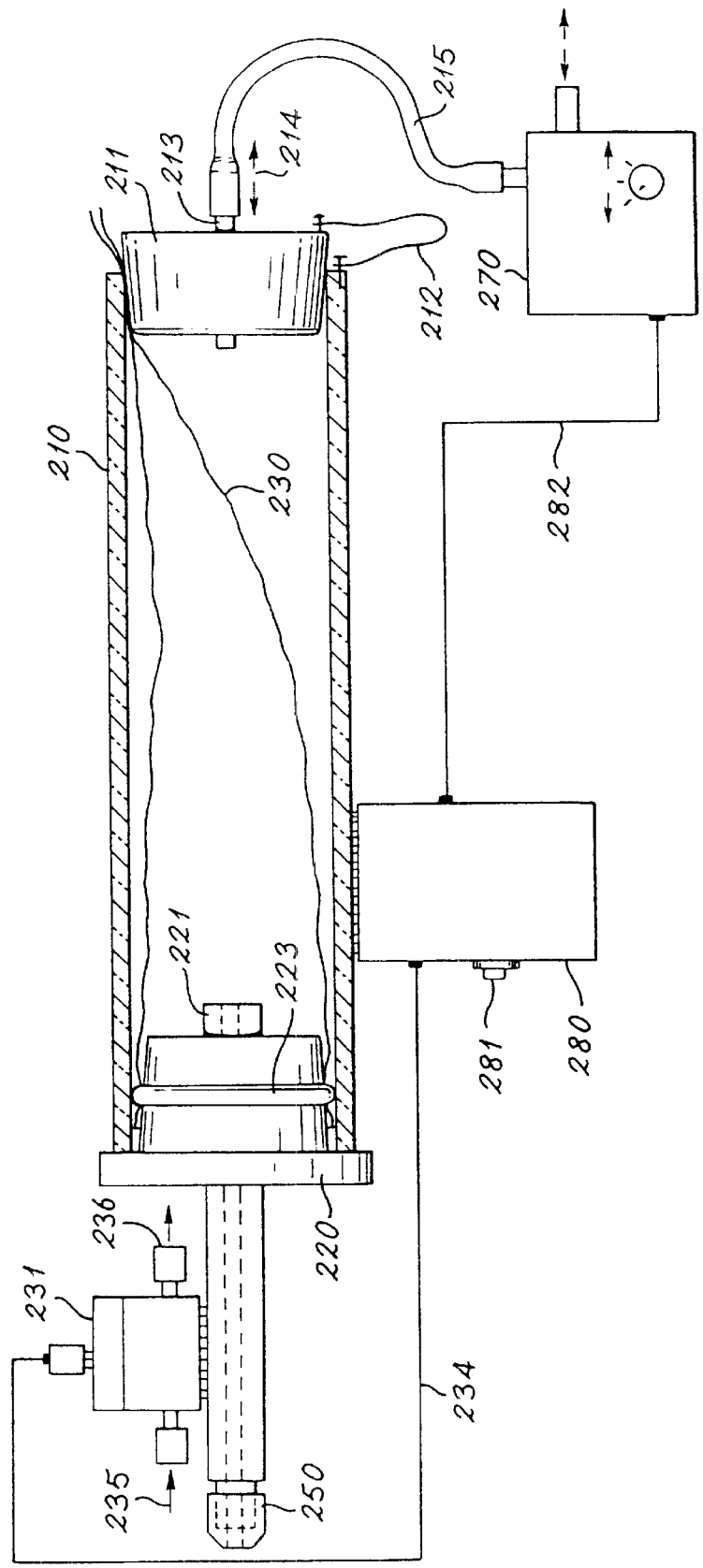
FIG. 4 shows a diagram of a further monitor embodying the invention.

FIG. 4 shows schematically and in part-sectional form yet further monitor apparatus embodying the invention. In this embodiment a sample is collected under controlled conditions to be available for transfer to a sensor arrangement.

The apparatus in FIG. 4 is in some respects similar to that in FIG. 1 and similar components have the reference from FIG. 1 with the prefix "2". Only one tube, 221, passes through closure 220. The arrangements for the container 230 within tube 210, using O-ring 223 and closure 211, are similar to those for FIG. 1. The arrangement by which gas, such as air, can be withdrawn from or supplied to the space within tube 210 are similar to those in FIG. 1, with an additional feature, that the starting of the pump 270 to withdraw gas is controlled over conductor 282, as described below. Tube 221 has an adaptor or speculum 250 which is removable for cleaning and replacement at each use. Conveniently tube 221 and adaptor 250 are of polytetrafluoroethylene (PTFE).

Tube 221 has associated with it a flow sensor 231 to detect the action by an animal of breathing out so that breath passes from input port 235 to outlet port 236. The flow sensor can be adjacent to tube 221, as shown, or incorporated in it. A suitable sensor is that made by Honeywell Microswitch, type AWM 3300V, and available as Radio Spares (RS) part 407-596.

This device uses a thin film bridge structure over a cavity in a body of silicon. The output of the device is connected over conductor 234 to a control unit 280, to which control conductor 282 of the pump 270 is also connected. Control unit 280 includes a switch 281 which is operable to make the monitor "ready for use". The circuit arrangement of conductors 234, 282 and switch 281 is such that when switch 281 is operated by a user and a suitable flow through flow sensor 231 is detected pump 270 is enabled, via conductor 282, to withdraw air from tube 210.

In use the apparatus is fitted with a clean adaptor 250 and container 230 and pump 270 operated to compress container 230. The apparatus is then introduced into the nostril of the cow or other animal to be examined and the switch 281 operated. This action brings the apparatus into the "READY" state. When the animal exhales to cause flow through sensor 231 of adequate degree a signal from sensor 231 over conductor 236 cooperates with the existing "READY" state to move the apparatus into the "SAMPLE" state. This causes pump 270 to withdraw air from tube 210 causing container 230 to receive a sample from the breath exhaled by the animal. Conveniently the pump 270 is arranged to stop when most of the air has been drawn from tube 210, producing a consistent sample volume.

The apparatus is then removed from the animal, applied to a suitable sensor arrangement and the sample discharged into it using pump 270, again controlled to stop when the sample has been driven out. The sensor may be a conducting polymer electronic nose or an electronic nose of the Fox 2000 type, developed by Southampton University. Alternatively a gas chromatograph can be used. For comparison and calibration purposes a sample can be divided among such devices. Desirably the humidity of the sample is controlled to increase reliability and accuracy. To this end the sample can be passed over one surface of a humidity balancing membrane. Air of a selected relative humidity is passed over the other surface to produce a required sample humidity.

In another arrangement a monitor can be installed in the air extraction path from a manger. (Air extraction is used to remove moisture resulting from the high humidity of exhaled breath.) If a high level of acetone is present this can be used to give an alarm of risk of ketosis in the animal using the manger.

The techniques described above provide improved monitoring of animal condition by examination of animal exhalations of various forms.

Figure 5:
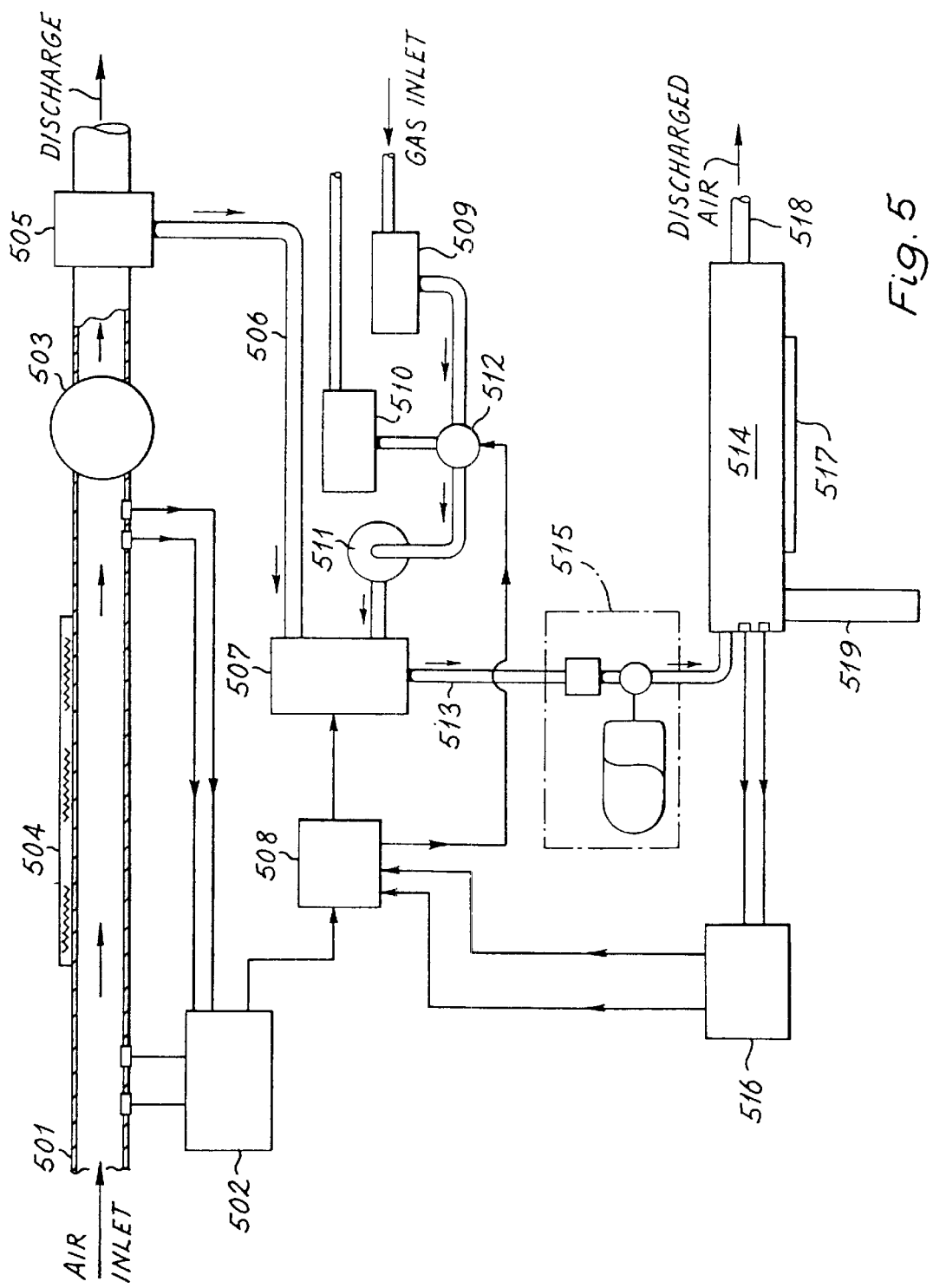
FIG. 5 shows a diagram of a further monitor embodying the invention.

FIG. 5 shows, schematically, an alternative form of the monitor embodying the invention. The temperature and humidity of animal exhalation entering the apparatus through the inlet 501 is monitored by sensors 502. The exhalation is propelled into the apparatus by use of pump 503 and its temperature adjusted by use of heating means 504 present in the flow path. A proportion of the exhalation is directed at valve 505 and the diverted sample is passed via tube 506 into a concentrating and mixing chamber 507 where it is mixed with calibration gas or other conveying medium as appropriate. The temperature and humidity of the sample in the mixing chamber 507 is monitored and controlled by a microprocessor 508. Use may be made of the drier 509, humidifier 510 and pump 511 to change the temperature and humidity of the sample in the mixing chamber. Valve 512 controls the relative proportions of dried and humidified calibration gas reaching chamber 507. When the temperature and humidity of the sample is within a specified value, the sample is passed via tube 513 into the sensing chamber 514 for analysis. Use of a cyclic pressure control system 515 may be made, if required, to control the pressure and velocity of the sample entering the sensing chamber 514. If used, the cyclic pressure control system is preferably itself controlled by the microprocessor 508. The temperature and humidity of the sample in the sensing chamber 514 is monitored by temperature and humidity sensors 516 which are in turn controlled by microprocessor 508. Sampling in chamber 514 is effected by the sensor array 517 and the output from the array is sent to microprocessor 508. The sample may be discharged from the apparatus via outlet 518 or it may be passed through via tube 519 to a gas chromatograph and/or mass spectrometer for further analysis.

What is claimed is:

1. An animal milking apparatus which includes an animal condition monitor comprising:

an inlet and an outlet for animal exhalation arising from said animal's milk, and for any medium in which said exhalation is conveyed;

a flow path between said inlet and outlet;

a component detector for identifying at least one of the presence and amount of one or more components of said exhalation;

one of an impeller and pump for one of directly and indirectly assisting flow of said exhalation and any medium in which said exhalation is conveyed;

a signal processor and power controller, wherein an output of the monitor provides in indication of a condition of said animal.

2. An animal milking line including:

a) a vessel for containing milk;

b) a vacuum connection to the vessel; and c) an animal condition monitor which comprises an inlet in communication with said vacuum connection; an outlet; a flow path between said inlet and outlet; a detector for identifying an odour, or for detecting the presence and/or amount of one or more components of vapour or other volatile materials emanating from milk contained in said vessel.

3. A method of monitoring a condition of an animal comprising: isolating vapour and/or volatile material emanating from said animal's milk and contacting a component detecting device with said vapour and/or volatile material, thereby producing a signal indicative of said condition of said animal.

4. A method according to claim 3 wherein said component detecting device comprises electrochemical detectors.

5. A method according to claim 3 wherein said animal condition is a metabolic condition.

6. A method according to claim 5 wherein said metabolic condition is oestrus, ketosis or mastitis.

* * * * *